United States Patent [19]
Knebelkamp et al.

[11] Patent Number: 5,637,746
[45] Date of Patent: Jun. 10, 1997

[54] PROCESS FOR PREPARING CARBOXYL-FUNCTIONAL SILANES AND SILOXANES

[75] Inventors: Arno Knebelkamp, Essen; Peter Lersch, Oberhausen; Christian Weitemeyer, Essen, all of Germany

[73] Assignee: Th. Goldschmidt AG., Essen, Germany

[21] Appl. No.: 636,508

[22] Filed: Apr. 25, 1996

[30] Foreign Application Priority Data

Apr. 29, 1995 [DE] Germany .................. 195 15 881.4

[51] Int. Cl.$^6$ .................................................. C07F 7/08
[52] U.S. Cl. ................................. 556/438; 556/439
[58] Field of Search ............................ 556/438, 439

[56] References Cited

U.S. PATENT DOCUMENTS 2,723,987  11/1955  Speier ........................... 556/438
3,109,011  10/1963  Pike et al. .................... 556/438

*Primary Examiner*—Paul F. Shaver
*Attorney, Agent, or Firm*—Anderson, Kill & Olick P.C.

[57] ABSTRACT

The invention relates to a process for preparing silanes or siloxanes having carboxyl functionalities, wherein a hydrogen silane or hydrogen siloxane compound is reacted with a tertiary butyl ester having an olefinic double bond and the sil(ox)ane-bonded tertiary butyl ester group is subsequently converted into the corresponding carboxyl group with elimination of isobutene.

12 Claims, No Drawings

PROCESS FOR PREPARING CARBOXYL-FUNCTIONAL SILANES AND SILOXANES

BACKGROUND OF THE INVENTION

The present invention concerns a process for preparing silanes or siloxanes (hereinafter abbreviated as sil(ox)ane) having carboxyl functionalities. This process is characterized in that a hydrogen silane or hydrogen siloxane compound is reacted with a tertiary butyl ester having an olefinic double bond, e.g. t-butyl methacrylate, in the presence of a transition metal catalyst and subsequent thereto the resulting sil(ox)ane-bonded tertiary butyl ester group is converted into the corresponding carboxyl group with elimination of isobutene. Particular advantages of this process are the solvent-free, single-stage synthesis, the high selectivities in respect of the yield of free carboxyl groups and that commercially available starting compounds are used.

Methods for preparing carboxyl-functional silanes or siloxanes are known and described, for example, in W. Noll: "Chemie und Technologie der Silicone" p. 142 ff. (2nd edition, Verlag Chemie, Weinheim 1968). Thus, SiH bonds can undergo hydrosilylation reactions with unsaturated carboxyl groups in the presence of known catalysts such as platinum compounds. The selectivity of such reactions is, however, very low, since the condensation of SiH and the acidic proton of the acid group with elimination of hydrogen takes place as a significant side-reaction and Si—O—C-linked structures are obtained. The hydrosilylation of acrylonitrile and subsequent acid-catalyzed hydrolysis likewise leads to carboxyl-functional sil(ox)anes. The disadvantage of this method is the use of the toxicologically problematical acrylonitrile and the presence of water which can result, particularly in the case of the siloxane derivatives, in undesired emulsion problems in the separation. In addition, a quantitative yield of free carboxyl groups can be obtained only with great difficulty. The same problems occur in the hydrolysis of addition products of unsaturated esters such as methyl methacrylate or trimethylsilyl methacrylate to sil(ox)anes.

Methods for introducing the carboxyl groups via Grignard processes (magnesium and $CO_2$ with, for example, Si—$CH_2$—Cl) or from carbonyl compounds having activated CH groups (malonic ester syntheses using haloalkylsiloxanes, e.g. Si—$CH_2$—Cl, and subsequent hydrolysis and decarboxylation) are not very suitable as industrial processes, since high demands have to be made of the purity of the starting materials and of the process equipment.

For the preparation of carboxyl-functional sil(ox)anes, it would be a considerable advantage if a solvent-free, single-stage and highly selective synthesis could be found.

BRIEF SUMMARY OF THE INVENTION

Surprisingly, it has now been found that the desired carboxyl-functional sil(ox)anes can be prepared in a simple manner by reacting a hydrogen silane or hydrogen siloxane compound with a tertiary butyl ester having at least one olefinic double bond and directly subsequent thereto converting the resulting sil(ox) ane-bonded tertiary butyl ester group into the corresponding carboxyl group with elimination of isobutene.

Such carboxyl-functional siloxanes are used, for example, for the preparation of aqueous silicone emulsions for the treatment of textile materials (described in U.S. Pat. No. 4,477,514) or as moisturizers in cosmetic formulations (described in U.S. Pat. No. 5,280,019).

DETAILED DESCRIPTION OF THE INVENTION

Examples of the compounds prepared according to the invention are:

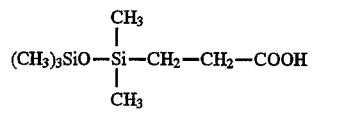

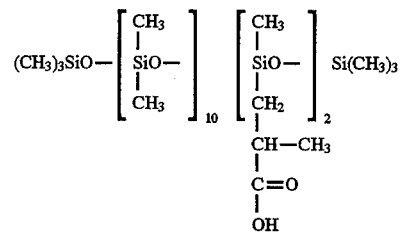

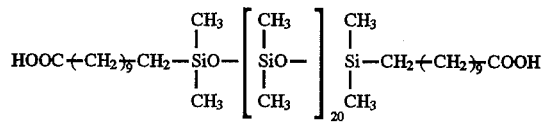

Suitable starting compounds include siloxanes of the general formula (A)

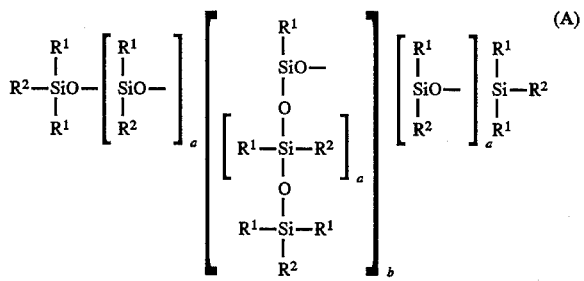

wherein the radicals $R^1$ are identical or different and each is an alkyl radical having from 1 to 4 carbon atoms or a phenyl radical, but with at least 90% of the radicals $R^1$ being methyl radicals, each $R^2$ is as defined for the radicals $R^1$ or is a hydrogen radical, but with at least one radical $R^2$ being a hydrogen radical, and the indices a in each occurrence is 0 to 100 and b in each occurrence is 0 to 5.

Silanes that can be used in the present invention include those of the formula (B)

where $R^a$, $R^b$ and $R^c$ in the molecule can be identical or different and each is a $C_1$ to $C_{18}$ aliphatic, aromatic, alkyloxy, or aryloxy radical, or a halogen radical.

The sil(ox)ane is reacted in the present invention under hydrosilylating conditions with one or more esters of the formula $H_2C=C(R^3)$—$C(O)O$-t-Bu, where $R^3$ is H or $CH_3$, or $H_2C=C(R^3)$—$R^4$—$C(O)O$-t-Bu, where $R^3$ is H or $CH_3$, and $R^4$ is an unbranched or branched and/or cyclic alkylene radical having from 1 to 30 carbon atoms. If desired, the carbon chain in $R^4$ can be interrupted by O or substituted by functional groups such as halogen or cyano.

Suitable esters are, in particular, t-butyl methacrylate, t-butyl acrylate and t-butyl undecenoate.

A suitable cyclic ester is, in particular, t-butyl norbornenecarboxylate.

The hydrosilylation reaction is known per se and comprehensively described, for example, in W. Noll: "Chemie und Technologie der Silicone" p. 45 ff. (2nd edition, Verlag Chemie, Weinheim 1968).

To prepare the t-butyl ester-functional sil(ox)anes, the hydrosilylation is carried out using equimolar amounts of the reactants, preferably in the presence of one or more transition metal catalysts, in particular platinum and rhodium compounds, at temperatures of from 60° to 140° C., preferably at from 80° to 130° C. and more preferably 100° to 130° C.

In the hydrosilylation reaction, the radical $R^2$ that is hydrogen in formula (A), and the hydrogen radical in formula (B), is replaced by —$CH_2C(R^3)$—$C(O)$-t-Bu or —$CH_2C(R^3)$—$R^4$—$C(O)O$-t-Bu. In the second step of the process of the present invention, the t-butyl ester protecting groups t-Bu are removed.

The removal of t-butyl ester protecting groups with elimination thereof as isobutene is likewise described in the literature. Among the many variants described, for the reaction with t-butyl ester-functional sil(ox)anes particular preference is given to those having a high catalytic activity. Examples of catalysts of this type are strong mineral acids, organic acids such as methanesulfonic acid or p-toluenesulfonic acid, and heterogeneous acidic catalysts such as aluminum silicates, zeolites and sheet silicates.

Depending on the type of catalyst used, the reaction temperature is from 60° to 120° C., preferably from 80° to 100° C.

The isobutene elimination can also be carried out in the presence of so-called Crivello salts (arylonium salts, e.g. diphenyliodonium trifluoromethanesulfonate or triphenylsulfonium hexafluorophosphate) which function as photochemical acid generators.

Furthermore, the elimination of the isobutene can also be carried out at temperatures above 160° C. without catalyst (thermal isobutene elimination).

Preparation and use examples:

EXAMPLE 1

109.5 g (0.77 mol) of t-butyl methacrylate together with 4 mg (=20 ppm of Pt) of hexachloroplatinic acid $H_2PtCl_6$ were placed in a 500 ml four-necked flask fitted with stirrer, dropping funnel, thermometer and reflux condenser and were heated while stirring to 110° C. At this temperature, 206.6 g (0.1 mol) of a laterally SiH-functionalized polydimethylsiloxane of the general formula $MD_{20}D^H{}_7M$ (Formula 1) and having a mean total chain length N=29 were added dropwise in such a way that, despite commencement of an exothermic reaction, a temperature of 130° C. was not exceeded. After addition was complete, the reaction mixture was stirred further for from 1 to 2 hours at 110° C., until monitoring of the conversion by means of the SiH value indicated that the methacrylate ester had been completely hydrosilylated. At a conversion of >99%, the reaction was stopped and the Pt catalyst residues were removed from the reaction mixture by filtration.

155 g (0.51 mol) of the t-butyl ester-functional siloxane (Formula 2) thus prepared were placed in a 250 ml four-neck flask fitted with stirrer, thermometer and reflux condenser, heated while stirring to 85° C. and at this temperature admixed with 1.94 g (1.25% by weight) of methanesulfonic acid as catalyst. During the reaction, a continuous elimination of isobutene could be observed. The decrease in the t-butyl ester groups as a function of time was followed by means of $^1$H-NMR spectroscopy and acid number determination. After a total reaction time of 1 hour, gas evolution could no longer be observed; the conversion according to acid number determination was 98%. NMR spectroscopy ($^1$H-, $^{13}$C-NMR: comparison of the signal intensities of the characteristic tert-butyl group) indicated a conversion of 97%. Filtration gave a yellow, liquid reaction product which had lateral carboxyl groups and according to the analytical results corresponded to the expected mean composition $MD_{20}D^{carboxyl}{}_7M$ (Formula 3).

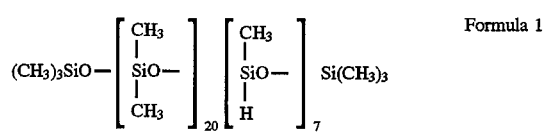

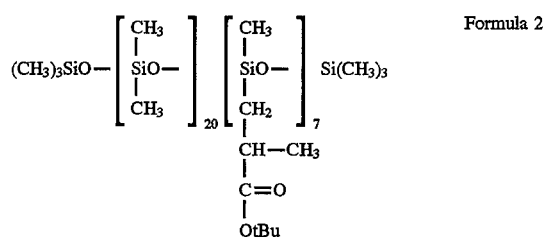

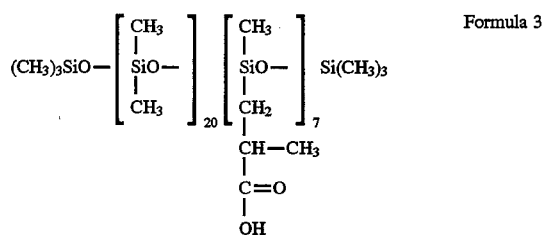

EXAMPLE 2

The procedure of Example 1 was repeated except that the removal of the Pt catalyst was omitted and, in a single-vessel process, p-toluenesulfonic acid monohydrate (2.5% by weight) was used in place of methanesulfonic acid. After a reaction time of 1 hour the conversion was 98% (NMR).

EXAMPLE 3

The procedure of Example 2 was repeated except that 4% by weight of calcium bentonite ("K 10", S üdchemie/acid-activated form) were added first and after a reaction time of 3 hours 1% by weight of methanesulfonic acid was additionally added. The reaction temperature was 100° C. After a total reaction time of 4 hours, the product was filtered. The acid number of the material obtained was 150, corresponding to a conversion of about 98%. $^1$H-NMR spectroscopy indicated a conversion of 100%.

EXAMPLE 4

Using a method similar to that described in Example 1, a t-butyl ester-functional siloxane of the general formula $M^{t\text{-}butyl\ ester}D_8M^{t\text{-}butyl\ ester}$ (Formula 4) and having a mean total chain length N=10 was prepared by the platinum-catalyzed addition of a corresponding SiH-siloxane to t-butyl methacrylate.

In a 250 ml four-necked flask fitted with stirrer, thermometer and reflux condenser, 82 g of the siloxane thus prepared (about 90 mmol) were heated while stirring to 100° C. and admixed with 0.82 g (1%) by weight) of calcium bentonite. The commencement of isobutene elimination could be recognized by means of a distinct gas evolution. After 3 hours, a further 0.82 g (1% by weight) of calcium bentonite were added and the mixture was left for a further 2 hours at the same temperature. The reaction mixture was subsequently filtered. The reaction conversion was monitored by determining the acid number. This was after a reaction time of 3 hours; an acid number of 130 was determined on the final product, corresponding to a conversion of >99% (Formula 5).

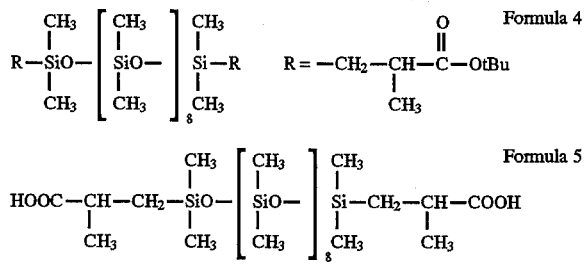

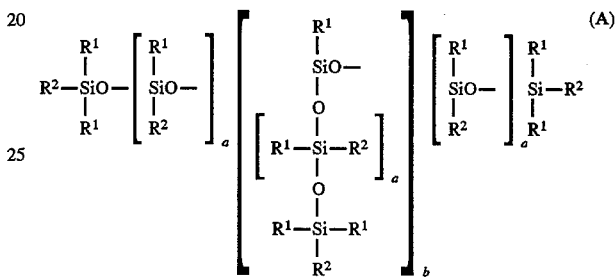

EXAMPLE 5

The procedure of Example 1 was repeated except that the removal of the protecting group was carried out using methanesulfonic acid (1% by weight, added once) in place of the calcium bentonite. The reaction temperature was 85° C., the reaction time was 1 hour; the conversion was determined as 98%.

EXAMPLE 6

The procedure of Example 1 was repeated except that calcium bentonite and methanesulfonic acid (each 1% by weight) were added together. At a reaction temperature of 100° C., the conversion after a reaction time of 1 hour was >99%.

Use Tests

To check the use properties of the modified carboxyl-functional polydimethylsiloxanes to be used according to the invention, their suitability as emulsifiers was studied. For this purpose, oils of different chemical nature were used and the concentration of the emulsifier used was varied.

For the test formulations, the corresponding oils were premixed with the emulsifier and the added amount of water was added in portions by means of a Dispermat while stirring and subjected to a visual examination. The results obtained for some test formulations are shown in the table below.

The composition of the mixtures was in each case:
Emulsifier (1 part), oil phase (4 parts), water (15 parts)
Evaluation criteria 1–5:
1=immediate separation
5=no separation
Emulsifier A=product from Example 1
Emulsifier B=product form Example 4

| Oil phase | Emulsifier A | Emulsifier B |
| --- | --- | --- |
| PDMS silicone oil (350 cP) | 2 | 3 |
| White oil 5E | 1–2 | 2 |
| Coconut oil | 4–5 | 3 |

The table indicates that the modified organopolysiloxanes to be used according to the invention have the desired use properties.

It is self-evident and clear to those skilled in the art that these examples represent only a selection of the existing possibilities and are in no way to be regarded as a restriction.

Thus, the method described naturally also makes it possible to obtain emulsifiers for w/o (water-in-oil) applications by appropriately increasing the number of carboxyl groups ($D^{carboxyl}$) while keeping the total chain length fixed.

We claim:

1. A process for preparing a silane or siloxane having carboxyl functionality, comprising (a) reacting the corresponding hydrogen silane or hydrogen siloxane with a tertiary butyl ester having an olefinic double bond and then (b) converting the tertiary butyl ester group on the product formed in step (a) into the corresponding carboxyl group and isobutene, and removing said isobutene.

2. A process according to claim 1, wherein step (a) is carried out using a hydrogen siloxane compound of the general formula (A)

where the radicals $R^1$ are identical or different and each is an alkyl radical having from 1 to 4 carbon atoms or a phenyl radical provided that at least 90% of the radicals $R^1$ are methyl radicals.

each $R^2$ is an alkyl radical having from 1 to 4 carbon atoms, a phenyl radical, or a hydrogen radical, but with at least one radical $R^2$ being a hydrogen radical, and a in each occurrence is 0 to 100 and b in each occurrence is 0 to 5.

3. A process according to claim 1, wherein step (a) is carried out using a hydrogen silane compound of the general formula (B)

$$R^a\text{—}\underset{\underset{R^c}{|}}{\overset{\overset{R^b}{|}}{Si}}\text{—}H \qquad (B)$$

where $R^a$, $R^b$ and $R^c$ in the molecule are identical or different and each is a $C_1$ to $C_{18}$ aliphatic, aromatic, alkyloxy, or aryloxy radical, or a halogen radical.

4. A process according to claim 1 wherein step (b) is carried out with one or more tert-butyl esters of the formula

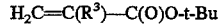

where $R^3$ is H or $CH_3$, or

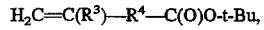

wherein $R^3$ is H or $CH_3$, and $R^4$ is an unbranched, branched or cyclic alkylene radical having from 1 to 30 carbon atoms and wherein $R^4$ is optionally interrupted by O or substituted by functional groups.

5. A process according to claim 2 wherein step (b) is carried out with one or more tert-butyl esters of the formula

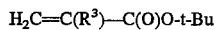

where $R^3$ is H or $CH_3$, or

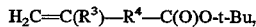

wherein $R^3$ is H or $CH_3$, and $R^4$ is an unbranched, branched or cyclic alkylene radical having from 1 to 30 carbon atoms and wherein $R^4$ is optionally interrupted by O or substituted by functional groups.

6. A process according to claim 3 wherein step (b) is carried out with one or more tert-butyl esters of the formula

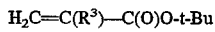

where $R^3$ is H or $CH_3$, or

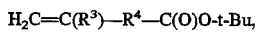

wherein $R^3$ is H or $CH_3$, and $R^4$ is an unbranched, branched or cyclic alkylene radical having from 1 to 30 carbon atoms and wherein $R^4$ is optionally interrupted by O or substituted by functional groups.

7. A process according to claim 1 wherein in step (a) the starting compounds are reacted in equimolar amounts at a temperature of from 60° to 140° C. in the presence of a transition metal catalyst.

8. A process according to claim 2 wherein in step (a) the starting compounds are reacted in equimolar amounts at a temperature of from 60° to 140° C. in the presence of a transition metal catalyst.

9. A process according to claim 3 wherein in step (a) the starting compounds are reacted in equimolar amounts at a temperature of from 60° to 140° C. in the presence of a transition metal catalyst.

10. A process according to claim 4 wherein in step (a) the starting compounds are reacted in equimolar amounts at a temperature of from 60° to 140° C. in the presence of a transition metal catalyst.

11. A process according to claim 5 wherein in step (a) the starting compounds are reacted in equimolar amounts at a temperature of from 60° to 140° C. in the presence of a transition metal catalyst.

12. A process according to claim 6 wherein in step (a) the starting compounds are reacted in equimolar amounts at a temperature of from 60° to 140° C. in the presence of a transition metal catalyst.

* * * * *